(12) United States Patent  (10) Patent No.: US 8,178,665 B2
Bódi et al.  (45) Date of Patent: May 15, 2012

(54) PROCESS FOR THE PRODUCTION OF EZETIMIBE AND INTERMEDIATES USED IN THIS PROCESS

(75) Inventors: József Bódi, Budapest (HU); János Éles, Budapest (HU); Katalin Szöke, Budapest (HU); Krisztina Vukics, Budapest (HU); Tamás Gáti, Budapest (HU); Krisztina Temesvári, Budapest (HU); Dorottya Kiss-Bartos, Albertirsa (HU)

(73) Assignee: Richter Gedeon Nyrt., Budapest (HU)

( * ) Notice: Subject to any disclaimer, the term of this patent is extended or adjusted under 35 U.S.C. 154(b) by 645 days.

(21) Appl. No.: 12/097,185

(22) PCT Filed: Dec. 18, 2006

(86) PCT No.: PCT/HU2006/000116
§ 371 (c)(1),
(2), (4) Date: Dec. 15, 2008

(87) PCT Pub. No.: WO2007/072088
PCT Pub. Date: Jun. 28, 2007

(65) Prior Publication Data
US 2009/0216009 A1    Aug. 27, 2009

(30) Foreign Application Priority Data
Dec. 20, 2005    (HU) ...................... 0501164

(51) Int. Cl.
*C07D 205/08* (2006.01)
*C07F 7/18* (2006.01)
*C07D 413/06* (2006.01)
*C07D 317/026* (2006.01)

(52) U.S. Cl. ........ 540/200; 549/454; 548/110; 548/229; 548/231

(58) Field of Classification Search .................... 540/200
See application file for complete search history.

(56) References Cited

U.S. PATENT DOCUMENTS
5,618,707 A    4/1997    Homann et al.
(Continued)

FOREIGN PATENT DOCUMENTS
WO    WO 97/12053    4/1997
(Continued)

OTHER PUBLICATIONS
Wu, et al., Journal of Organic Chemistry (1999), 64(10), 3714-3718.*
(Continued)

*Primary Examiner* — Mark Berch
(74) *Attorney, Agent, or Firm* — Jason D. Voight

(57) ABSTRACT

A process for the production of 1-(4-3(R)-[3(S)-(4-fluorophenyl)-3-hydroxypropyl]-4(S)-(4-hydroxyphenyl)-2-azetidinone (ezetimibe) according to the following reaction scheme: (I), (II), (III), (IV), (V), (VI), (VII), (VIII), (IX), (X), (XI) where the substances of the general Formulas II, IV, VI, VIII, IX, X and XI are new, Formula III is a non-isolated intermediate, R1, R2 and R3 are represented by the compounds of Formulas Va-Vd, (Va), (Vb), (Vc), (Vd) and R4 is a silyl, e.g., tert-butyl-dimethyl-silyl, tert-butyl-diphenyl-silyl group.

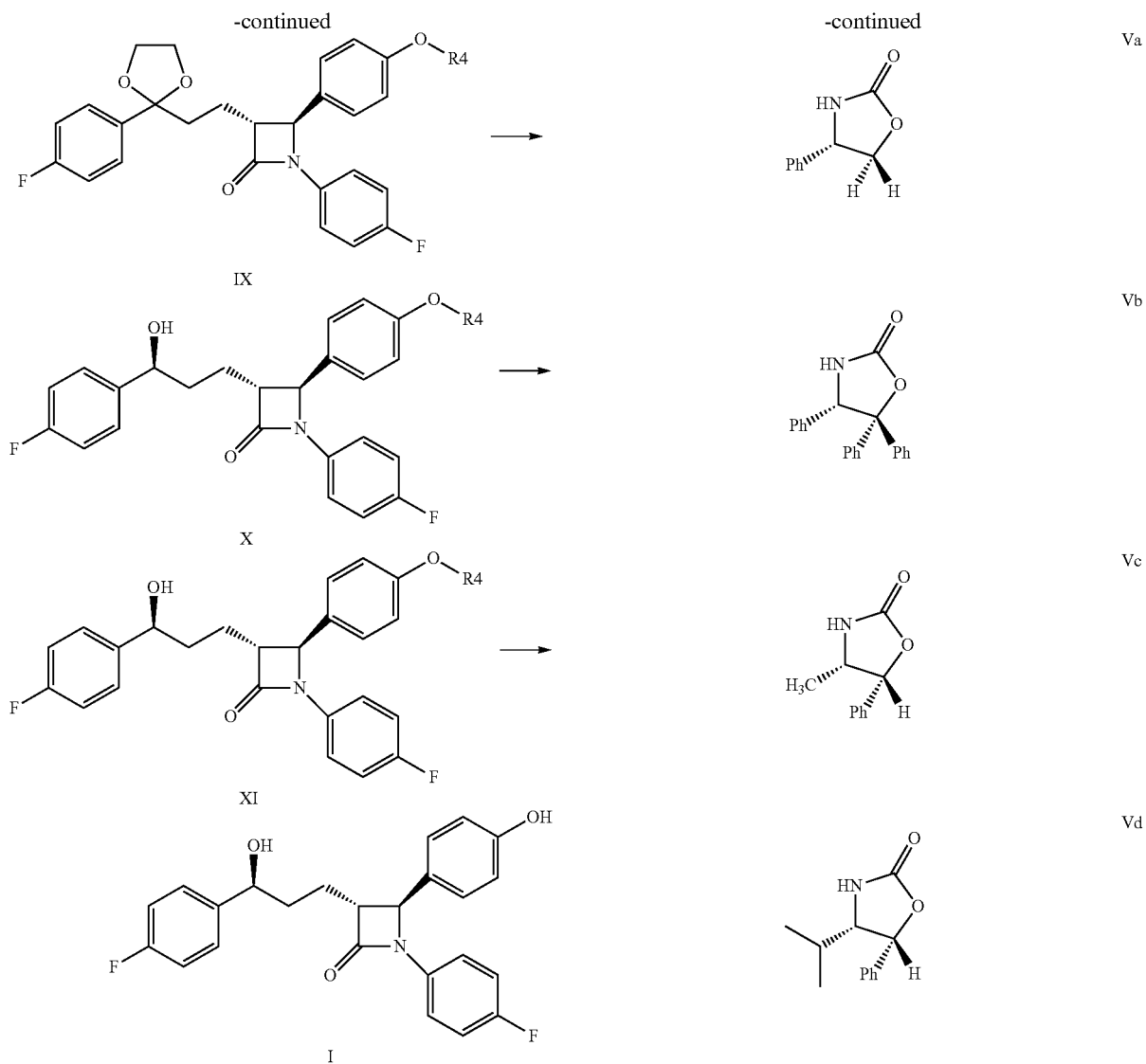
10 Claims, No Drawings

U.S. PATENT DOCUMENTS

| | | | |
|---|---|---|---|
| 5,739,321 | A | 4/1998 | Wu et al. |
| 5,767,115 | A | 6/1998 | Rosenblum et al. |
| 5,856,473 | A | 1/1999 | Shankar |
| 5,886,171 | A | 3/1999 | Wu et al. |
| 5,919,672 | A | 7/1999 | Homann et al. |
| 6,133,001 | A | 10/2000 | Homann et al. |
| 6,207,822 | B1 | 3/2001 | Thiruvengadam et al. |
| 6,627,757 | B2 | 9/2003 | Fu et al. |
| 2008/0032964 | A1* | 2/2008 | Kansal et al. ............ 514/210.02 |
| 2008/0058305 | A1* | 3/2008 | Kansal et al. ............ 514/210.02 |
| 2008/0318920 | A1* | 12/2008 | Czarnik .................. 514/210.02 |
| 2009/0047716 | A1* | 2/2009 | Perlman et al. ............... 435/121 |
| 2009/0048441 | A1* | 2/2009 | Reddy et al. .................. 540/200 |
| 2009/0093627 | A1* | 4/2009 | Szabo et al. .................. 540/200 |
| 2009/0227786 | A1* | 9/2009 | Gavalda I Escude et al. 540/200 |
| 2010/0010212 | A1* | 1/2010 | Kansal et al. ................. 540/200 |
| 2010/0168414 | A1* | 7/2010 | Escude et al. ................. 540/200 |
| 2011/0046389 | A1* | 2/2011 | Stepankova et al. .......... 548/230 |

FOREIGN PATENT DOCUMENTS

| | | |
|---|---|---|
| WO | WO 00/34240 | 6/2000 |
| WO | WO 2005/066120 A2 | 7/2005 |
| WO | WO 2008089984 A2 * | 7/2008 |
| WO | WO 2008106900 A1 * | 9/2008 |
| WO | WO 2009067960 A2 * | 6/2009 |
| WO | WO 2009140932 A2 * | 11/2009 |

OTHER PUBLICATIONS

Corey et al., Highly Enantioselective Borane Reduction of Ketones Catalyzed by Chiral Oxazaborolidines . . . , J.Am.Chem.Soc., 1987, vol. 109, pp. 5551-5553.

* cited by examiner

PROCESS FOR THE PRODUCTION OF EZETIMIBE AND INTERMEDIATES USED IN THIS PROCESS

This is the National Stage of International Application PCT/HU2006/000116, filed Dec. 18, 2006.

FIELD OF THE INVENTION

This invention relates to a new process for the preparation of ezetimibe, i.e., 1-(4-)-3(R)-[3(S)-(4-fluorophenyl)-3-hydroxypropyl]-4(S)-(4-hydroxyphenyl)-2-azetidinone of Formula I. Furthermore the invention relates to novel intermediates used in this process.

BACKGROUND OF THE INVENTION

In the developed countries a significant part of deaths is caused by the cardiovascular disorders. These diseases are mostly triggered by the atherosclerotic alteration of the coronary arteries. Among the risk factors for development of the illness as the high blood pressure, diabetes, smoking etc. the most important is the high concentration of cholesterol in the serum. The active ingredients and formulations decreasing concentration of the serum cholesterol are useful agents in treating and preventing atherosclerosis.

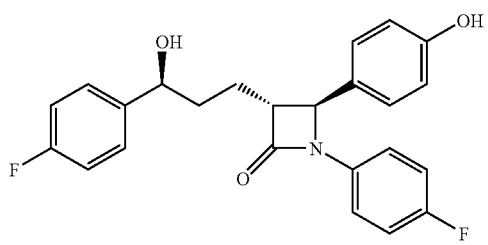

I

Ezetimibe, i.e., 1-(4-fluorophenyl)-3(R)-[3(S)-(4-fluorophenyl)-3-hydroxypropyl]-4(S)-(4-hydroxyphenyl)-2-azetidinone of Formula I is the active ingredient of some up-to-date marketed pharmaceutical preparations having significant hypocholesterolemic effect used in the treatment and preventing of atherosclerosis, disclosed in U.S. Pat. No. 5,767,115 (Schering Co. U.S.A.) and European Patent No. 720,599

The first synthetic methods for the preparation of ezetimibe and relatives were published in these descriptions. According to one of their methods the appropriate trans-azetidinone derivative is prepared in one step with the reaction of [4-(benzyloxy)-benzylidene]-(4-fluorophenyl)-amine and methyl-4-(chloro-formyl)-butyrate base, and after hydrolysis and forming an acid chloride with the given 3-[2-(4-benzyl-oxy-phenyl)-1-(4-fluorophenyl)-4-oxo-azetidin-3-yl]-propionyl-chloride (4-fluorophenyl)-zinc-chloride is acylated in the presence of tetrakis(triphenyl-phosphine) Palladium. The pure 1-(4-fluorophenyl)-3(R)-[3-oxo-3-(4-fluorophenyl)-propyl)]-4(S)-(4-benzyloxy-phenyl)-2-azetidinone is obtained by chiral HPLC separation, that the end-product ezetimibe is prepared from by subsequent enantioselective reduction and cathalytic hydrogenation. In this method the substituted azetidinone ring was not formed by an enantioselective method, therefore the last but one intermediate is purified by a chiral column chromatographic method. In this manner at least 50% of a late intermediate is lost significantly increasing the costs of procedure.

To avoid the costly chiral chromatography a microbiological and an enzymatic separation method were introduced in U.S. Pat. No. 5,919,672 (Schering Co.). Although the microbiological method decreases the costs of resolving of the racemate, but even in this manner the yield of resolvation can not be increased above 50%.

In the European Patent No. 720,599 (Schering Co.) the preparation methods of some tri-substituted azetidinone derivatives having hipocholesterinemic activity are disclosed. For forming of the β-lactame ring a one-step and a two-step method are described and the building-up of the aril-hydroxy-alkyl side-chain is carried out by several methods. For the synthesis of ezetimibe an enantioselective method is revealed. First the azetidinone ring is formed in a two-step synthesis from 5-oxo-5-((S)-2-oxo-4-phenyl-oxazolidine-3-yl)-pentane acid methyl ester and [4-(benzyloxy)-benzylidene]-(4-fluorophenyl)-amine. An acylation is carried out with the aid of the obtained 3-[(2S,3R)-2-(4-benzyl-oxy-phenyl)-1-(4-fluorophenyl)-4-oxo-azetidin-3-yl]-propionyl-chloride in the presence of (4-fluorophenyl)-zinc-chloride tetrakis(triphenyl-phosphine)-palladium. The given 1-(4-fluorophenyl)-3(R)-[3-oxo-3-(4-fluorophenyl)propyl)]-4(S)-(4-benzyloxy-phenyl)-2-azetidinone intermediate is purified by column chromatography, then the active ingredient is obtained after an enantioselective reduction of the oxo group, and removing of the protecting group.

From the former procedures a strategically different method was published in the International Application No. WO 97/45,406 and in U.S. Pat. No. 5,739,321 (Schering Co). According to these publications enantioselective forming of the trans-substituted azetidinone intermediate is carried out by a reaction of 4(S)-hydroxy-butyrolactone and a protected imine in the presence of a base, then the 3-(4-fluorophenyl)-3-hydroxypropyl side chain is built up in a several-step synthesis through the mentioned 1-(4-fluorophenyl)-3(R)-[3-oxo-3-(4-fluorophenyl)-propyl)]-4(S)-(4-benzyloxy-phenyl)-2-azetidinone intermediate. The benzyl protecting group is removed by catalytic hydrogenation.

Another reaction pathway is disclosed in U.S. Pat. No. 5,856,473. (Schering Co.). According to the description (3R, 4S)-4-(4-benzyloxy-phenyl)-1-(4-fluorophenyl)-3-[(E)-3-(4-fluorophenyl)-allyl]-azetidin-2-one including a double bond in the side chain is prepared alkylating with 1-(4-fluorophenyl)-4(S)-(4-benzyl-oxy-phenyl)-2-azetidinone 4-fluorocinnamyl-bromide, or with an enantioselective synthesis starting from (S)-3-[5-(4-fluorophenyl)-pent-3-enoil]-4-phenyl-oxazolidine-2-one. 1-(4-fluorophenyl)-3(R)-[3-oxo-3-(4-fluorophenyl)propyl)]-4(S)-(4-benzyloxy-phenyl)-2-azetidinone intermediate is obtained with oxydating the side chain, from which the end-product ezetimibe is obtained after removing of the protecting group by the enantioselective reduction mentioned.

These enantioselective procedures are common in the subsequent using of multi-step synthesis methods with the optically pure azetidinone derivatives prepared with the relative costly enantioselective synthesis procedures. The key intermediate, 1-(4-fluorophenyl)-3(R)-[3-oxo-3-(4-fluorophenyl)propyl)]-4(S)-(4-benzyloxy-phenyl)-2-azetidinone is purified only by chromatography increasing significantly the costs of the industrial methods.

In the Patent Applications No. WO 2000/34,240 (Schering Co.) and in No. WO 1995108,532 and in the European Patent No. 0,720,599 (Schering Co.) an improved and more effective and enantioselective ezetimibe synthesis pathway is discovered. According to the procedure first 3-[(S)-5-(4-fluorophenyl)-5-hydroxy-pentanoyl]-oxazolidine-2-one is prepared in 98% de (diastereomer excess) purity from the appropriate oxo-compound with an enantioselective reduction. 3-[(S)-5-(4-fluorophenyl)-5-hydroxy-pentanoyl]-oxazolidine-2-one and N-(4-hydroxy-benzylidene)-4-fluoroanilin are silylated in situ with chlorotrimethylsilane in one vessel. The appropriate β-amino-amid product is prepared by treating the obtained mixture with TiCl$_4$ reagent in the presence of a base using a procedure well-known in the art. The authors experienced surprising stability of the trimethylsilyl protecting group of phenolic OH group. In spite of the stability of the silyl group the intermediate could be isolated only with a 65% yield after work-up and further silylation step. Ezetimibe is obtained after cyclisation of the β-amino-amide followed by removing of the protecting groups. In this procedure formation of the 3(S)-hydroxy group with relatively costly enantioselective method is carried out at the beginning of the synthesis then the product is isolated after further reaction steps and purification procedure.

Stereoselective forming of the 3(S)—OH group is one of the key steps preparing ezetimibe. Each of the mentioned procedures applies one of the versions of the enantioselective reduction methods catalysed by CBS-oxazaborolidine, well-known from the literature (E. J. Corey et al., J. Am. Chem. Soc. 1987, 109, 5551-5553). The achieved de-value (diastereomer excess) is 88-98%, as it expected typically.

U.S. Pat. Nos. 5,886,171 and 5,856,473 (Schering Co.) describe an enantioselective reduction method using CBS-oxazaborolidine catalyst, in which the protected 1-(4-fluorophenyl)-3(R)-[3-oxo-3-(4-fluorophenyl)propyl)]-4(S)-(4-hydroxyphenyl)-2-azetidinone is converted to protected 1-(4-fluorophenyl)-3(R)-[3(S)-hydroxy-3-(4-fluorophenyl)propyl)]-4(S)-(4-hydroxyphenyl)-2-azetidinone.

U.S. Pat. Nos. 6,207,822 and U.S. Pat. No. 6,627,757 (Schering Co.) describe application of similar reducing agents and chiral catalysts for converting of 3-[5-(4-fluorophenyl)-5-oxo-pentanoyl]-4(S)-4-phenyl-1,3-oxazolidine-2-one to 3-[5(S)-5-(4-fluorophenyl)-5-hydroxy-pentanoyl]-4(S)-4-phenyl-1,3-oxazolidine-2-one.

In U.S. Pat. No. 5,618,707 and in Patent Application No. WO 1997/12,053 (Schering Co.) another possibility of enantoselective reduction is described, in which an early intermediate 3-[5-(4-fluorophenyl)-5-oxopentanoyl]-4(S)-4-phenyl-1,3-oxazolidine-2-one is converted by a stereoselective microbiological reduction to 3-[5(S)-5-(4-fluorophenyl)-5-hydroxypentanoyl]-4(S)-4-phenyl-1,3-oxazolidine-2-one.
The achieved de-value≧95% (diastereomeric excess) is similar to that of the value obtained by the CBS-oxazaborolidine catalysis.

In U.S. Pat. No. 6,133,001 a stereoselective microbiological reduction is describe for conversion of 1-(4-fluorophenyl)-3(R)-[3-oxo-3-(4-fluorophenyl)propyl)]-4(S)-(4-hydroxyphenyl)-2-azetidinone into 1-(4-fluorophenyl)-3(R)-[3(S)-hydroxy-3-(4-fluorophenyl)propyl)]-4(S)-(4-hydroxyphenyl)-2-azetidinone (ezetimibe). The end-product is prepared in a small quantity, and it is purified by preparative thin-layer chromatography.

In the International Application No. WO 2005/066,120 (Ranbaxy Ltd.) the enantioselective reduction of the oxo group of 3-[5-(4-fluorophenyl)-5-oxo-pentanoyl]-4(S)-4-phenyl-1,3-oxazolidine-2-one and of 1-(4-fluorophenyl)-3(R)-[3-oxo-3-(4-fluorophenyl)propyl)]-4(S)-(4-hydroxyphenyl)-2-azetidinone are performed by (−)-B-chloro-diisopinocampheyl-borane achieving a selectivity similar to CBS-reduction. However, it is interesting that in this manner in the reduction of 20 g 1-(4-fluorophenyl)-3(R)-[3-oxo-3-(4-fluorophenyl)propyl)]-4(S)-(4-hydroxyphenyl)-2-azetidinone as little as 3 g ezetimibe end-product is obtained after a column-chromatographic purification.

SUMMARY OF THE INVENTION

This invention provides a novel, industrially easily realizable and economical process comprising only few steps, and built on new intermediates for the production of 1-(4-3(R)-[3(S)-(4-fluorophenyl)-3-hydroxypropyl]-4(S)-(4-hydroxyphenyl)-2-azetidinone (ezetimibe) according to the following reaction scheme:

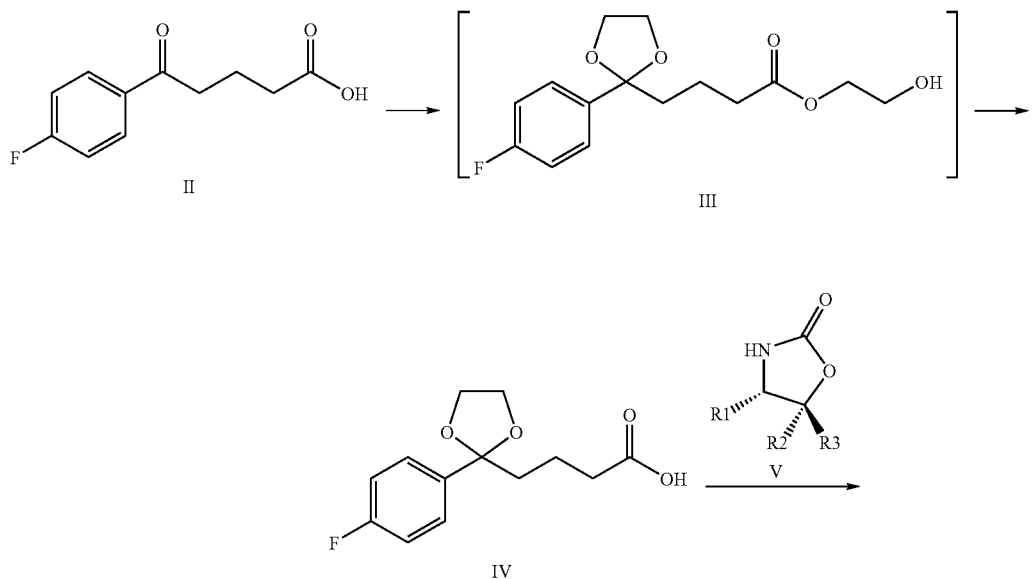

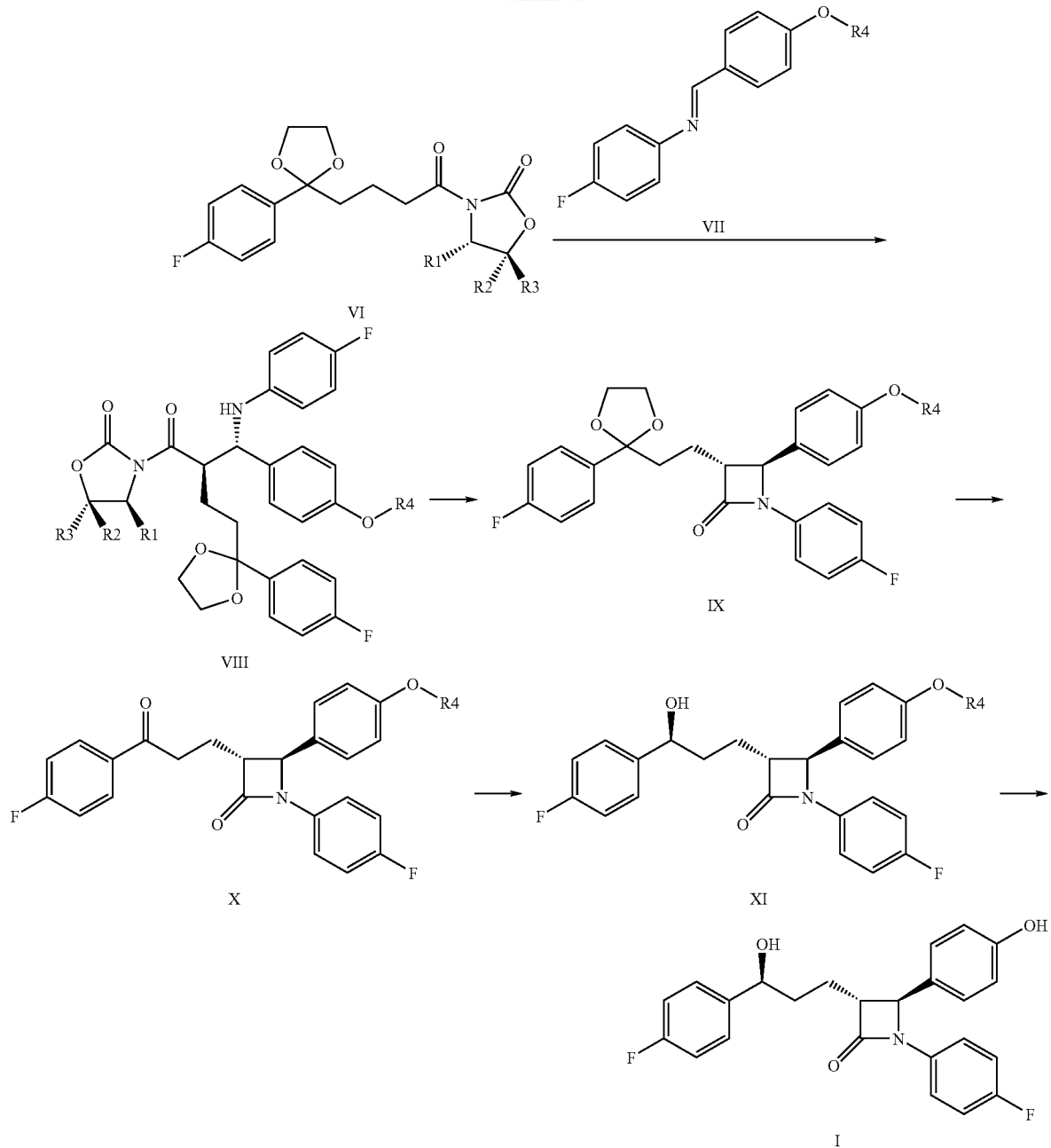
wherein
- the substances of the general Formulas II, IV, VI, VIII, IX, X and XI are new
- Formula III is a non-isolated intermediate
- R1, R2 and R3 are represented by the compounds of Formulas Va-Vd,
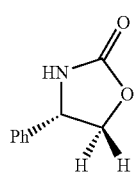
Va
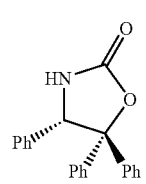
Vb
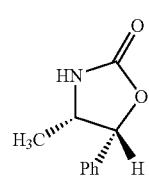
Vc Vd

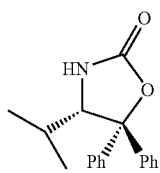

and R4 is a silil, e.g. tert.buthyl-dimethyl-silil, tert-buthyl-diphenyl-silil group.

DETAILED DESCRIPTION OF THE INVENTION

Taking into consideration the drawbacks of the known ezetimibe synthetic procedures, we strived to work out an industrial-scale, safe production method comprising economic simple technological steps, providing an active ingredient with purity fulfilling Pharmacopoeias' requirements. We determined to work out a synthetic strategy that do not comprises tedious technological steps or ones requiring extreme circumstances, and where the intermediates can be produced by simple procedures with high efficiency and can be isolated in high purity. For the protection of the functional groups we strived to apply such protection groups that are stabile during the synthesis, can be built in simple and cheap ways and remove them selectively. We intended to carry out the more expensive technological steps at the end of the synthesis, and to regain the expensive auxiliary materials (e.g. optically active ones).

During our experiments we experienced surprisingly that in the following synthesis pathway with using a special protection group combination in most cases such excellent intermediates are obtained that can easily be purified in simple ways and at high efficiencies, owing to their outstanding crystallizing ability. The non-crystallizing intermediates could be applied in the next steps without purification. A new reaction not published in the literature before, was discovered, where a stereoisomer compound, formed as a side-product in the Ti(IV)-catalyzed Mannich type reaction, could be converted into the desired intermediate.

The procedure of our invention applying new intermediates comprises seven steps that are listed below.

Step 1:

4-(4-fluoro-benzoyl)-butyric acid (II) is converted into 4-[2-(4-fluoro-phenyl)-[1,3]dioxolane-2-yl]-butyric acid (IV) trough a not-isolated intermediate compound (III).

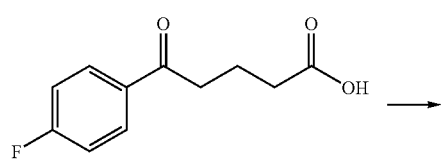

Step 2:

A chiral oxazolidinone (V) is acylated with 4-[2-(4-fluoro-phenyl)-[1,3]dioxolane-2-yl]-butyric acid (IV) to obtain the oxazolidinone derivative (VI)

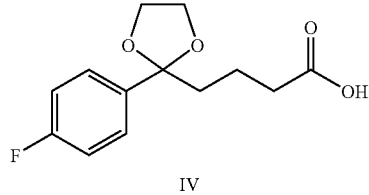

wherein R1, R2 and R3 are represented in the following structures (Va-Vd):

-continued

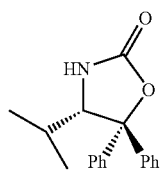

Vd

Step 3:

The following acylated oxazolidinone (VI) is reacted with an imine (VII) and a compound of Formula (VIII) is isolated,

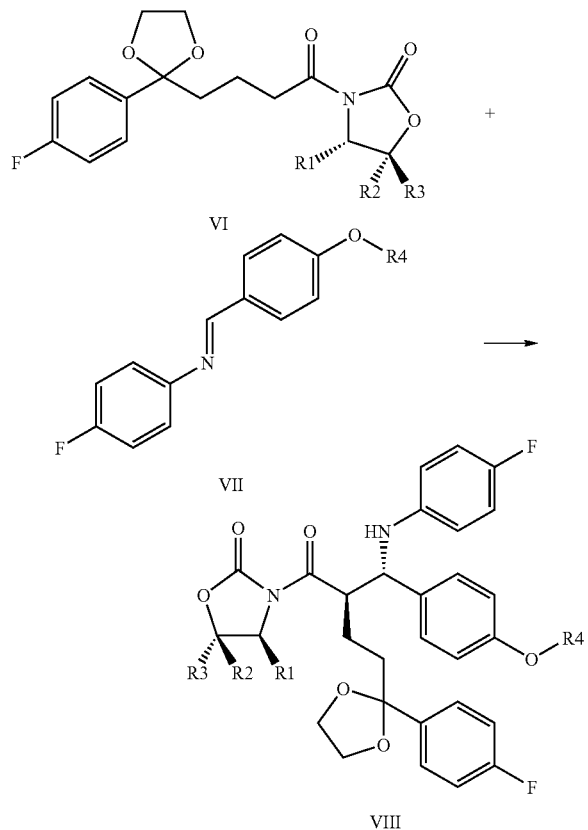

where R4 represents a silil, e.g. tert-butyl-dimethyl-silil (TBDMS), tert-butyl-diphenyl-silil group.

Step 4:

The protected azetidinone (IX) is obtained by cyclisation of the compound of Formula (VIII).

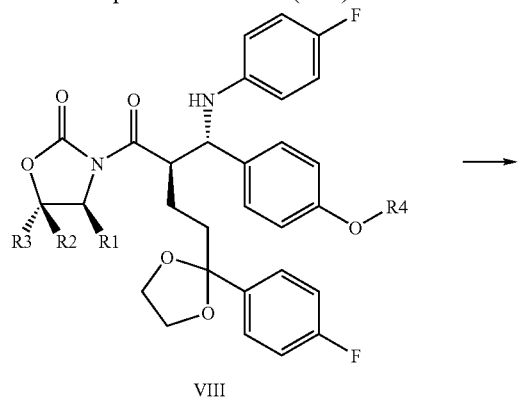

VIII

-continued

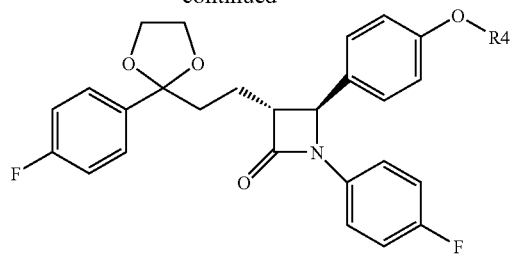

IX

Step 5:

The compound of Formula (X) is obtained with hydrolysing of the ketal group of the compound of Formula (IX).

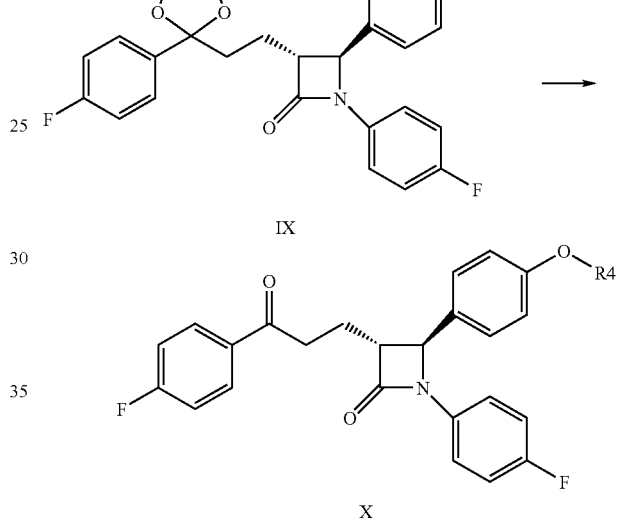

Step 6:

With an enantioselective reduction of the compound of Formula X the compound of Formula XI is obtained.

Step 7:

Removing the silil protecting group of the compound of Formula XI the end-product, ezetimibe is obtained (I).

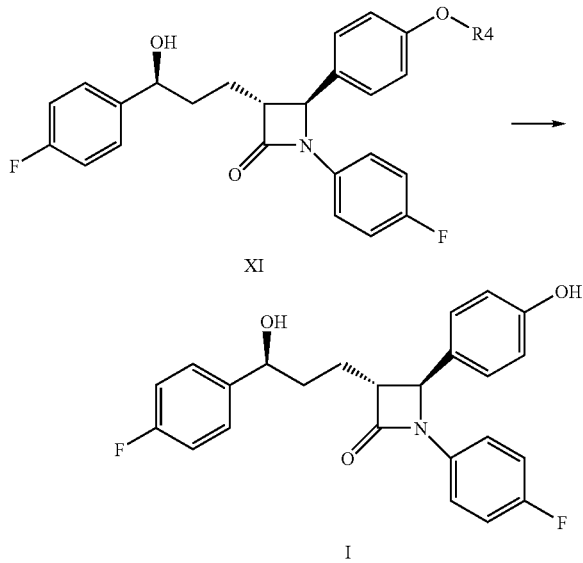

In the following part all of the steps are detailed:

Step 1:

In an inert water-free solvent, e.g. in dichloromethane in the presence of a strong acid, e.g. conc. sulphuric acid or p-toluene sulphonic acid, preferably conc. sulphuric acid and water-binding auxiliary material, e.g. trimethyl-ortho-formiate 4-(4-fluor-benzoil)-butyric acid (II) is reacted in one step with ethylene glycol at a 20-25° C. temperature. The reaction is stopped with addition of a base, e.g. NaHCO$_3$. The solvent is changed to an alcoholic one, preferably to methanol, and the formed ester intermediate (III) is hydrolyzed by a base solution, preferably with potassium hydroxide solution. The formed 4-[2-(4-fluoro-phenyl)-[1,3]dioxolane-2-yl]-butyric acid (IV) is isolated after the concentration of the reaction mixture, then acidification with a weak acid, e.g. with tartaric acid, citric acid, preferably citric acid followed an extraction with an appropriate solvent, e.g. ethyl acetate. The product is purified by crystallization from an apolar solvent, e.g. from n-hexane or n-heptane.

Step 2:

The product of Step 1 is converted into a mixed anhydride in an inert water-free solvent, e.g. in tetrahydrofurane, or dichloro methane, preferably in tetrahydrofurane using 1-1.7 times molar quantity, preferably 1.05-1.10 equivalent acid-chloride, e.g. pivaloil chloride in the presence of triethyl amine at a temperature between −20 and −10° C. An oxazolidinone of the Formula V, preferably S-(+)-4-phenyl-2-oxazolidinone (Va) is added into the solution of the mixed anhydride obtained, in the presence of an appropriate activating reagent, e.g. litium chloride (LiCl) or 4-dimethyl-amine-piridin, preferably litium chloride, then the solution is stirred for 4-8 h at a temperature between −20 and 25° C. The product is isolated by extraction and purified by crystallisation.

Step 3:

Method A:

The product of Step 2 is reacted with an imine of Formula VII (where R4 represent preferably tert-butyl-dimethyl-silil group) in an inert water-free solvent, e.g. dichloromethane, and N$_2$ atmosphere at a temperature between −40 and −25° C. in the presence of TiCl$_4$ and Ti(IV)-isopropoxyde, and in the presence of tertiary base, e.g. diisopropyl-ethyl-amine for 1-2 h. The reaction is stopped with an alcohol, preferably isopropyl alcohol, and the product (VIII) is isolated by extraction, and after evaporation is purified stirring it with methanol.

For the protection of the phenolyc hydroxyl a silil type protecting group, preferably tert-butyl-dimethyl-silil group is used, that is especially advantageous comparing with other silil type groups inclined to split in even milder circumstances, and with other alkyl and acyl type protecting groups. Since the tert-butyl-dimethyl-silil protecting group is stabile under the synthetic circumstances, there is no need to resililise the intermediate before isolation, that during the working-up partly lost its protecting group. Moreover the tert-butyl-dimethyl-silil protecting group can easily be removed with an acidic treatment avoiding side reactions. On the other hand for removing of benzyl type protecting groups requires either a technologically more tedious and more dangerous catalytic hydrogenation or a stronger acidic removal process. Unfortunately the carbenium cation, that forms during the splitting of benzyl and alkyl type protecting groups in acidic media, results in significant quantity of by-products with alkylation of the phenyl ring. As it is well-known from the literature, the removal of the acyl-type protecting groups with a base is accompanied by considerable side-reactions (e.g. opening the lactame ring).

Our experiments proved that in the Ti(IV)-catalysed Mannich-type equilibrium reaction beyond the expected R4=tert-butyl-dimethyl-silil product (VIIIa) an isomer side product (VIIIb) also forms in a considerable extent. We demonstrated that starting from (VIIIa) and (VIIIb) under the reaction circumstances mentioned the same products are obtained as in case the reaction starting from (VIa) and (VIIa). With the suitable selection of the experimental parameters the equilibrium can be shifted to the direction favourable of forming (VIIIa) product, and it can be isolated with a 73-78% yield.

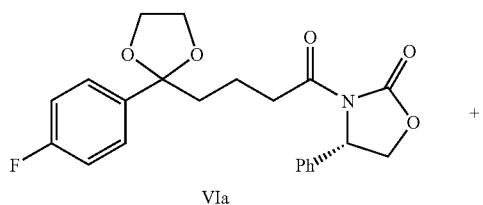

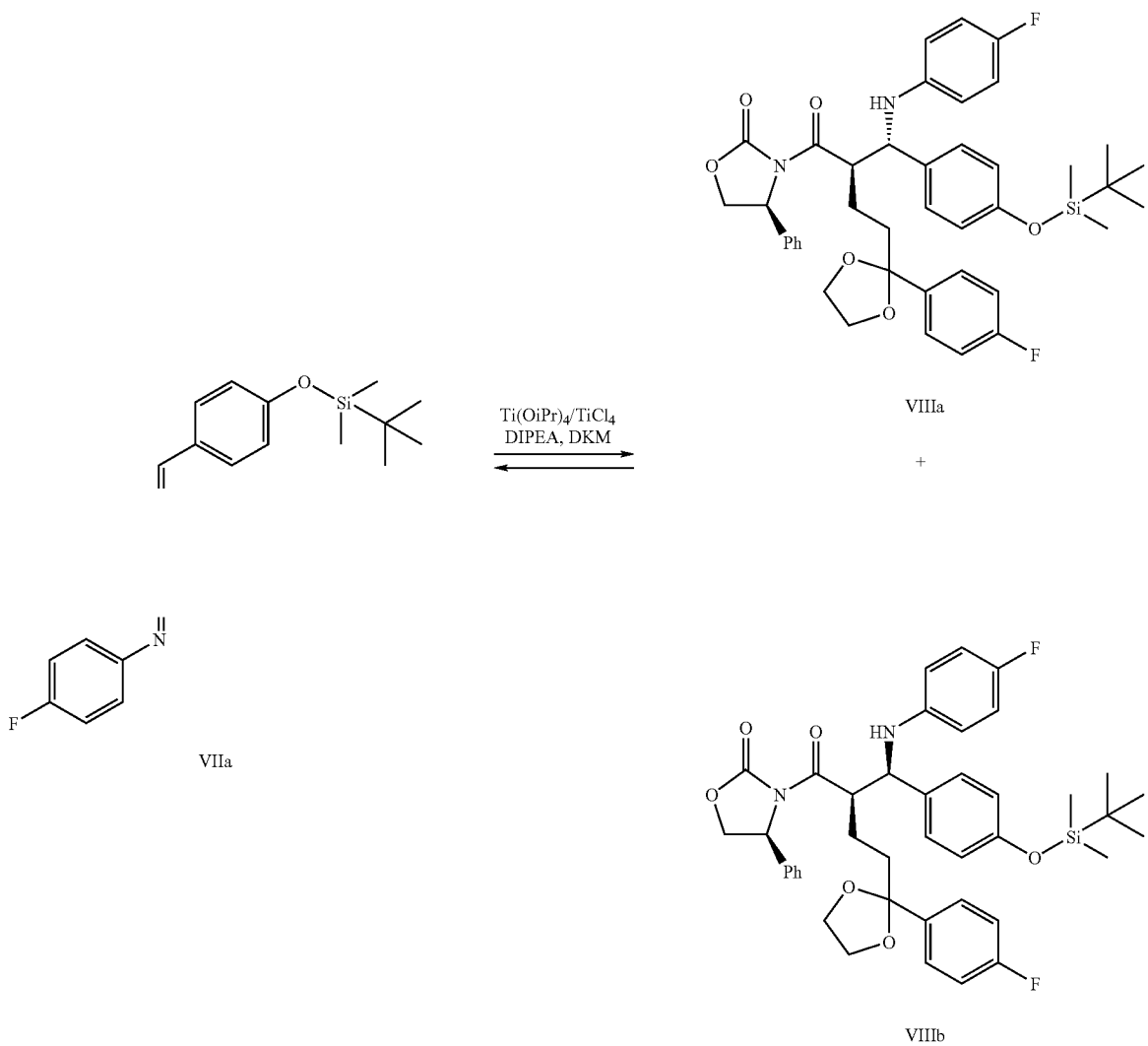

The (VIIIb) isomer, that may be present in the mother liquor obtained after filtering the product from the methanolic suspension, can be converted into (VIIIa) under the circumstances of the Ti(IV)-catalysed Mannich-type reaction. In this way yield of the reaction can be increased considerably.

For these purpose the methanolic mother liquor is evaporated, the solvent is changed for an appropriate one, e.g. toluene, the solution is decolorized by silica gel, and then after filtering it is evaporated. Using this procedure, from this mixture a further product of Formula VIII can be obtained as follows:

The evaporation residue is solved in dichloromethane, and in the presence of Ti(IV)-isopropoxyde and a tertiary base, e.g. diisopropyl-ethyl-amine, the solution is stirred under an inert atmosphere, e.g. $N_2$, at a temperature between −40 and −25° C. for 1-2 h. The pure product of Formula VIIIa is isolated with the method described above.

Method B:

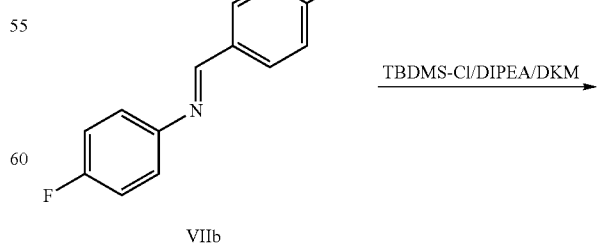

-continued

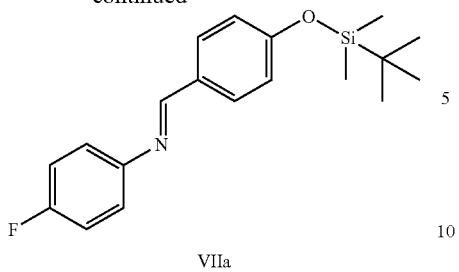

VIIa

In an alternative procedure first the compound of Formula VIIIa is produced in-situ in dichloromethane in the presence of diisopropyl-ethyl-amine (DIPEA) with the reaction of (E)-(4-hydroxy-benzylidene)-(4-fluorophenyl)-amine (VIIb) and tert-butyl-dimethyl-silil-chloride (TBDMS-Cl), then the solution of the obtained product of Formula VIIa is used according to the description in Method A.

Step 4:

The product of Step 4 of Formula VIII is sililated in an appropriate solvent, e.g. tetrahydrofurane, toluene, methyl-tert-butyl-ether, or acetonitril, preferably in acetonitril, with a suitable sililating agent, e.g. with bis(trimethyl-silil)-acetamide, at a temperature between 20 and 25° C., for 1-3 h. A fluoride compound, preferably tetrabutylammonium-fluoride-trihydrate is added to the mixture, in a catalytic quantity (0.1-10 mol %), preferably in 0.5-1 mol %. This cyclisation reaction mixture is stirred further for 0.5-3 h, preferably for 0.5 h, then the reaction is stopped by water, and the product of Formula IX is isolated with an alkane-type solvent, e.g. with n-hexane. The chiral auxiliary material S-(+)-4-phenyl-2-oxazolidinone (Va) formed back from the acetonitrilic phase, following its concentrating, is extracted with dichloromethane, and purified by crystallisation.

Step 5

The compound of Formula IX obtained in Step 4 is treated in an inert solvent, e.g. dichloromethane with an acidic-type clay mineral, preferably with Montmorillonite at a temperature 20-25° C., for 3-6 h. Under these circumstances tert-butyl-dimethyl-silil protecting group is stabile, and the ketal protecting group can be selectively removed. The so obtained product of Formula X is separated with a simple filtering, and after evaporation it is purified by crystallisation.

Step 6:

In our procedure the enantioselective reduction for forming the 3-(S)-hydroxyl group is carried out at the end of the synthesis. In this way the specific expenditure of the expensive chiral catalyst is less. As the asymmetry center is built in an optically pure uniform isomer, the purification of the end-product is simplified to the separation of two diastereomeres. Accordingly, the so obtained compound of Formula X in Step 5 is reduced with a borane-type reduction agent, e.g. with borane-dimethyl-sulphide, borane-tetrahydrofuran, borane-diethyl-anilin, or katechol-borane, preferably with a mixture of borane-dimethyl-sulphide and borane-tetrahydrofurane, in the presence of a chiral CBS-oxazaborolidine-type catalyst, well-known for this purpose, in an inert solvent, e.g. dichloromethane, in inert atmosphere, e.g. in $N_2$ at a temperature between −20 and 20° C., preferably between −5 and +5° C. A chiral CBS-oxazaborolidine (compounds XIIa-XIId), preferably oxazaborolidine (compound XIIa) is used as a catalyst.

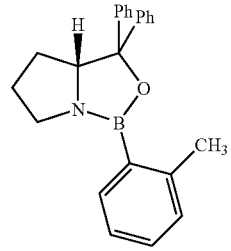

XIIa

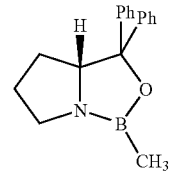

XIIb

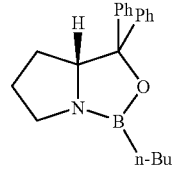

XIIc

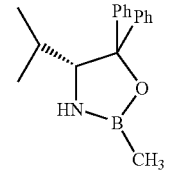

XIId

The product is isolated by extraction and taken further into the next reaction without purification.

Step 7:

The so obtained product of Formula XI is heated with a mixture of diluted aqueous hydrochloric or sulphuric acid solution, preferably with sulphuric acid solution and an alcoholic solvent, e.g. methanol or iso-propyl alcohol, preferably iso-propyl alcohol, at a temperature between 50-70° C., for 1-3 h. The end-product is crystallized from the reaction mixture with adding water, then it is purified by recrystallisation. The advantages of the present invention are summarized as follows:

a) In our procedure in the new pathway based on new compounds, the key intermediates, owing to their excellent crystallising ability, can effectively be purified in simple crystallising operations.

b) For the protection of phenolic OH group a silile-type, preferably tertiary butyl-dimethyl-silil group is used, which is more advantageous than other, in milder circumstances easily, splitting ones, e.g. in comparing with alkyl- and acyl-type groups.

c) In an enantioselective Ti(IV)-catalysed Mannich-type reaction the appropriate intermediate (VIIIa) is produced at a high yield (85-90%), however, the stereoisomeric by-product is not lost in the equilibrium reaction, but it is mostly converted into the wanted intermediate, d) therefore, the most part of the chiral auxiliary, S-(+)-4-phenyl-2-oxazolidinone (>70% of the introduced quantity) is regenerated with a simple method during the synthesis.

e) In the procedure the enantioselective reduction for forming the 3-(S)-hydroxyl group is carried out at the end of the synthesis. In this way the specific expenditure of the expensive chiral catalyst is less. As the asymmetry center is built in an optically pure uniform isomer, the purification of the final product is simplified to the separation of two diastereomeres.

Summarising, in our invention such a new procedure is discovered, that is suitable for the economic production of ezetimibe in industrial scale. The purity of the active ingredient obtained by this procedure can meet the today's more and more demanding quality requirements of the pharmaceutical active ingredients.

EXAMPLES

The following examples are illustrative and are not meant to limit the scope of the claimed invention.

Example 1

Preparation of 4-[2-(4-fluoro-phenyl)-[1,3]dioxolane-2-yl]-butyric acid (IV)

21.0 g (0.1 mol) 4-(4-fluor-benzoil)-butyric acid (II) was weighed into a 500 ml round-bottom flask and suspended in 210 ml dichloro methane. During continuous stirring 28 ml (31.2 g, 0.5 mol) ethylene-glycol, 32 ml (31.04 g, 0.3 mol) trimethyl-ortho-formiate, and 0.5 ml conc. sulphuric acid is added dropwise into the suspension. The reaction mixture was stirred at 20-25° C. for 3-6 h. The reaction was analytically controlled by thin-layer chromatography. When the ketone came to an end, as its spot disappeared by thin-layer chromatography, the reaction was stopped with adding 5 g solid NaHCO$_3$. The suspension was stirred for 05 min., then the solvent is removed by evaporation, and the residue is solved in 150 ml methanol. This solution was cooled in an icy water-bath, and during the cooling 100 ml 10% NaOH solution was added. The flask was closed and the turbid mixture was stirred at 20-25° C. for about 1 h. The hydrolysis was analytically controlled by thin-layer chromatography. When the ester came to an end, as its spot disappeared by thin-layer chromatography, the methanol was removed by vacuum evaporation, and during intensive cooling in an icy water-bath, 350 ml 10% citric acid solution was added to the residue to achieve an acidic pH-value between 3-4. The precipitated product was extracted with 200 ml ethyl acetate. The aqueous phase was extracted twice with 50-50 ml ethyl acetate, and then the united organic phase was washed to neutral with 5×50 ml water. The ethyl acetatic solution was dried on anhydrous Na$_2$SO$_4$, the desiccant was filtered out, and the filtrate was evaporated in vacuum. The evaporating residue is crystallized with addition of 50 ml n-hexane at 0° C. The crystalline material of (IV) is isolated by filtration, and is dried.

Yield: 23 g, (90%)
Melting point: 65-67° C.
$^1$H NMR data: (500 MHz, DMSO-d$_6$, 25° C.) δ 1.41-1.52 (m, 2H), 1.79-1.87 (m, 2H), 2.18 (t, J=7.5 Hz, 2H), 3.63-3.73 (m, 2H), 3.91-4.01 (m, 2H), 7.13-7.22 (m, 2H), 7.37-7.45 (m, 2H), 11.97 (brs, 1H) ppm.

Example 2

Preparation of (S)-3-{4-[2-(4-Fluorophenyl)-[1,3]dioxolane-2-yl]-butyril}-4-phenyl-oxazolidine-2-one (VIa)

42 g (165 mmol) compound Formula IV, product of Example 1 was solved in 340 ml water-free terahydrofurane, and the vessel was rinsed by dry N$_2$ gas. The solution was cooled to −20° C., and 55 ml (390 mmol) triethyl-amine was added. A mixture of 40 ml tetrahydrofurane and 20.2 ml pivaloyl chloride (19.8 g, 164 mmol) is added trough a drip-funnel for some 30 min at a temperature between −10° C. and −20° C. The precipitate-containing mixture was stirred for 2 h at a temperature between −10 and −20° C., and then 24.45 g (150 mmol) solid S (+)-4-phenyl-2-oxazolidinone (Va) and 7.5 g (177 mmol) water-free litium-chloride was sprinkled consecutively into it. Then the suspension was stirred for 4 h while it warmed up to 20-25° C.

The reaction was analytically controlled by thin-layer chromatography. When the spot of S (+)-4-phenyl-2-oxazolidinone decreased to 3%, the reaction was stopped with adding 300 ml toluene and 150 ml saturated ammonium-chloride solution. The phases were separated then the aqueous phase was extracted by 50 ml toluene. The united toluenic solution is washed by 2×150 ml 10% citric acid solution, 2×150 ml 1M NaOH solution and at last with 3×150 ml water. The organic phase was dried on anhydrous Na$_2$SO$_4$, the desiccant was filtered out, and the filtrate was evaporated in vacuum. The residue was crystallized at 0° C. with 150 ml isopropyl-alcohol. The product (VIa) was dried in vacuum in the presence of P$_2$O$_5$.

Yield: 55.7 g (93%)
Melting point: 100-102° C.
$[\alpha]_D^{25}$=+54.3°, (c=1, dichloromethane)
$^1$H NMR data: (500 MHz, DMSO-d$_6$, 25° C.) δ 1.42-1.56 (m, 2H), 1.76-1.85 (m, 2H), 2.80 (dt, J=17.2, 7.5 Hz, 1H), 2.90 (dt, J=17.2, 7.5 Hz, 1H), 3.61-3.71 (m, 2H), 3.89-3.99 (m, 2H), 4.13 (dd, J=8.7, 3.6 Hz, 1H), 4.71 (t, J=8.7 Hz, 1H), 5.43 (dd, J=8.7, 3.6 Hz, 1H), 7.12-7.19 (m, 2H), 7.23-7.28 (m, 2H), 7.29-7.34 (m, 1H), 7.34-7.42 (m, 4H) ppm.

Example 3

Preparation of (S)-3-{(R)-2-[(S)-[4-(tert-butyl-dimethyl-silanyl-oxy)-phenyl]-(4-fluoro-phenyl-amine)-methyl]-4-[2-(4-fluoro-phenyl)-[1,3]dioxolane-2-yl]-butyric}-4-phenyl-oxazolidine-2-one (VIIIa)

Preparation of Titanium-Trichloride-Isopropoxyde Reagent:
0.95 ml (0.9 g, 3.2 mmol) Ti(IV)-isopropoxyde was added into a solution of 0.99 ml (1.71 g, 9 mmol) TiCl$_4$ made in 34 ml dichloromethane at 0° C. temperature and N$_2$-atmosphere. The mixture was stirred for 15 min. at 0° C. This solution was used in the following coupling step.
Coupling (Method A)
4.0 g (10 mmol) compound of Formula VIa and 6.6 g (20 mmol) imine compound of Formula VIIIa are weighed into a 250 ml vessel supplied with a magnetic stirrer, a thermometer, a drip-funnel and a N2-inlet, and solved in 50 ml dichloromethane. The mixture is cooled to −40° C. and 3.6 ml (20.7 mmol) DIPEA was added. The titanium-trichloride-isopropoxyde reagent solution is gradually added trough the drip-funnel for about 30 min. The mixture is stirred for 1 h at a temperature between −30 and −40° C., then the reaction was stopped by adding 25 ml isopropyl-alcohol and 50 ml dichloromethane at a temperature between −30 and −40° C., and after it was stirred for further 30 min. at the same temperature. The so obtained orange suspension was poured slowly into 100 ml pH=7 tartarate buffer, then after 15 min's stirring the phases were separated. The aqueous phase was extracted with further 3×30 ml dichloromethane, then the united dichloromethanic solution was washed with 30 ml water, dried with anhydrous Na$_2$SO$_4$, the desiccant was filtered out and the filtrate was evaporated in vacuum. 50 ml methanol was added to the residue, the so obtained suspension was stirred at 20-25° C. for 10 min, and then the product was isolated by filtering. The white crystalline compound (VIIIa) was dried in vacuum in the presence of $P_2O_5$.

Yield: 5.5 g (76%)

Coupling (Method B)

25.8 g (120 mmol) (E)-(4-hydroxy-benzylidene)-(4-fluorophenyl)-amine is weighed into a 2 l vessel supplied with a magnetic stirrer, a thermometer, a drip-funnel and a N2-inlet, it was solved in 500 ml dichloromethane, then 57.8 ml (332 mmol) diisopropyl-ethyl-amine (DIPEA)—was added at 20-25° C. 19.9 g (132 mmol) tert-butyl-dimethyl-silil-chloride was added and the solution was stirred at 20-25° C. for 1-2 h.

The reaction was analytically controlled by thin-layer chromatography. When the spot of the starting material, (E)-(4-hydroxy-benzylidene)-(4-fluorophenyl)-amine disappeared from the chromatogram, 40 g of (100 mmol) (VIa) compound was added, and the mixture was cooled to a temperature between −25 and −30° C. In some 30 min period through the drip-funnel the solution of 9.5 ml (9 g, 32 mmol) titanium-tetraisopropoxide and 9.9 ml (17.1 g, 90 mmol) titanium-tetrachloride ($TiCl_4$) in 340 ml dichloromethane at 0° C. was gradually added. The mixture is stirred for 0.5 at a temperature between −25 and −30° C., then the reaction in the mixture was stopped by adding 250 ml isopropyl alcohol and 500 ml dichloromethane at a temperature between −30 and −40° C., and after it was stirred for further 30 min. at the same temperature. The so obtained mixture was poured slowly into 1000 ml pH=7 tartarate buffer, then after 15 min's stirring the phases were separated. The aqueous phase was extracted with further 3×250 ml dichloromethane, then the united dichloromethanic solution was washed with 300 ml water, dried with anhydrous $Na_2SO_4$, the desiccant was filtered out and the filtrate was evaporated in vacuum. 500 ml methanol was added to the residue, the so obtained suspension was stirred at 20-25° C. for 10 min, and then the product was isolated by filtering. The white crystalline compound (VIIIa) was dried in vacuum in the presence of $P_2O_5$.

Yield: 57 g (78%)

Melting point: 211-213° C.

$[\alpha]_D^{25}=-0.9°$, (c=1, dichloromethane)

$^1$H NMR data: (500 MHz, $CDCl_3$, 25° C.) δ 0.17 (s, 6H), 0.97 (s, 9H), 1.22-1.35 (m, 1H), 1.66-1.90 (m, 3H), 3.58-3.77 (m, 2H), 3.84-3.96 (m, 2H), 4.21 (dd, J=8.7, 2.9 Hz, 1H), 4.26 (d, J=9.1 Hz, 1H), 4.46-4.57 (m, 1H), 4.66 (t, J=8.7 Hz, 1H), 5.06 (brm, 1H), 5.44 (dd, J=8.7, 2.9 Hz, 1H), 6.33-6.41 (m, 2H), 6.65-6.78 (m, 4H), 6.91-6.98 (m, 2H), 7.02-7.13 (m, 6H), 7.13-7.19 (m, 1H), 7.25-7.31 (m, 2H) ppm.

Reworking of the Mother Liquor

The obtained methanolic mother liquor was evaporated the solvent was changed for 200 ml toluene. 10 g silica gel Si 60 was added to the toluenic solution, the suspension was stirred at 20-25° C. for 15 min. Silica gel was filtered out, washed with toluene, and the filtrate was evaporated. The evaporation residue was solved in 100 ml dichloromethane, the mixture was cooled to −30° C., and 7 ml (40 mmol) DIPEA was added in $N_2$-atmosphere. 2 ml titanium-trichloride-isopropoxide reagent solution made from (1.9 g, 6.74 mmol) titanium-tetraisopropoxide and 1.81 ml (3.12 g, 16.3 mmol) $TiCl_4$ was added trough the drip-funnel in a 30 min. period. The reaction mixture was stirred at a temperature between −30 and −40° C., than the pure product of Formula VIIIa is isolated in the same manner as in case of the coupling reaction.

Yield: 8.0 g. United yield: 65 g (89%)

Example 4

Preparation of (3R,4S)-4-[4-(tert-butyl-dimethyl-silanyl-oxy)-phenyl]-1-(4-fluorophenyl)-3-{2-[2-(4-fluorophenyl)-[1,3]dioxolane-2-yl]-ethyl}-azetidin-2-one (IX, R4=TBDMS)

20.25 g (28 mmol) compound of Formula VIIIa was suspended in 556 ml water-free acetonitrile at 20-25° C., then 13.6 ml (56 mmol) N,O-bis(trimethylsilil)-acetamide was added. The reaction mixture was stirred at 20-25° C. for 2 h, then, 0.1 g (0.28 mmol) tetrabutyl-ammonium-fluoride-trihydrate was added, and stirred further at the same temperature. At the end of the reaction (0.5-1 h) the suspension turns to a clear solution. The reaction was analytically controlled by thin-layer chromatography. When the spot of the open chain amine compound starting material (VIIIa) disappears, the reaction mixture was diluted with 556 ml water and 556 ml n-hexane. Following the separation of the phases the aqueous acetonitrile phase was extracted with 556 ml n-hexane. The united n-hexane phase was dried with anhydrous $Na_2SO_4$, the desiccant was filtered out, the filtrate was evaporated in vacuum. The so obtained compound (IXa) is oil that is used up without purification in the next reaction step.

$^1$H NMR data: (500 MHz, DMSO-$d_6$, 25° C.) δ(ppm) 0.16 (s, 3H), 0.16 (s, 3H), 0.92 (s, 9H), 1.70-1.82 (m, 2H), 1.89-2.09 (m, 2H), 3.07 (td, J=7.7, 2.3 Hz, 1H), 3.62-3.72 (m, 2H), 3.91-4.01 (m, 2H), 4.85 (d, J=2.3 Hz, 1H), 6.80-6.86 (m, 2H), 7.07-7.22 (m, 6H), 7.24-7.29 (m, 2H), 7.38-7.43 (m, 2H) ppm.

Regenerating of S (+)-4-phenyl-2-oxazolidinone, Formed Back as a By-Product, from the Aqueous Acetonitrile Phase:

The acetonitrilic water phase obtained as above was concentrated to about 500 ml volume, and the product precipitated from the residue was extracted with 2×100 ml dichloromethane. The united dichloromethane solution was evaporated, the residue was crystallized from a mixture of ethyl acetate and n-hexane. The regenerated S (+)-4-phenyl-2-oxazolidinone was isolated by filtration.

Yield: some 3.9 g (some 85%, calculated to VIIIa introduced)

Example 5

Preparation of (3R,4S)-4-[4-(tert-butyl-dimethyl-silanyl-oxy)-phenyl]-1-(4-fluorophenyl)-3-[3-(4-fluorophenyl)-3-oxo-propyl]-azetidin-2-one (X, R4=TBDMS)

About 17 g compound obtained according to Example 4 (IX, R4=TBDMS) (content at least: 15.8 g, 28 mmol) was dissolved in 330 ml dichloromethane, 42 g Montmorillonite K10 was added at 20-25° C. The heterogeneous mixture was stirred at 20-25° C. for 2-4 h. The reaction was analytically controlled by thin-layer chromatography. Having disappeared the spot of the starting material in the chromatogram, the reaction mixture was filtered, the Montmorillonite K10A that was filtered out washed first with 50 ml dichloromethane, and then 3×50 ml mixture of dichloromethane and methanol (2:1 v/v). The united filtrate was evaporated the residue was crystallized from a mixture of ethanol and water at 0° C.

Yield: 11.6 g dried product (80%, together the steps 4. and 5.)

Melting point: 110-112° C.

$[\alpha]_D^{25}=+4.0°$, (c=1, dichloromethane)

$^1$H NMR data: (500 MHz, DMSO-$d_6$, 25° C.) δ 0.16 (s, 3H), 0.17 (s, 3H), 0.93 (s, 9H), 2.12-2.23 (m, 2H), 3.14-3.30

(m, 3H), 4.99 (d, J=2.3 Hz, 1H), 6.81-6.88 (m, 2H), 7.10-7.18 (m, 2H), 7.20-7.27 (m, 2H), 7.29-7.38 (m, 4H), 7.99-8.07 (m, 2H) ppm.

Example 6

Preparation of (3R,4S)-4-[4-(tert-Butyl-dimethyl-silanyl-oxy)-phenyl]-1-(4-fluorophenyl)-3-[(S)-3-(4-fluorophenyl)-3-hydroxypropyl]-azetidin-2-one (XIa)

5.00 g (9.6 mmol) (3R,4S)-4-[4-(tert-butyl-dimethyl-silanyl-oxy)-phenyl]-1-(4-fluorophenyl)-3-[3-(4-fluorophenyl)-3-oxo-propyl]-azetidin-2-on was solved in 9.6 ml water-free dichloromethane, and then 1.92 ml (0.96 mmol) (R)-o-tolyl-CBS-oxazaborolidine 0.5 M-toluenic solution was added. The mixture was cooled to a temperature between 0 and −5° C., and at this temperature a dichloromethanic solution of 1.9 ml 1.0 M borane-dimethyl was added for 6 h. The reaction mixture had been stirred at this temperature until the spot of the starting keton disappeared according to the thin-layer chromatographic investigation. Then 10 ml methanol, 0.5 ml 5% hydrogen-peroxide solution, and 10 ml 2M sulphuric acid were added. Having been stirred the mixture for 0.5 h, the phases were separated. The organic phase was washed with 50 ml 2N sulphuric acid and then 50 ml 5% sulphite-solution. The solution was dried on anhydrous sodium-sulphate, filtered and evaporated.

Yield: 5.05 g colourless oil.

Diastereomer excess: >98% de (chiral HPLC)

$^1$H NMR data: (500 MHz, DMSO-$d_6$, 25° C.) δ 0.17 (s, 3H), 0.18 (s, 3H), 0.93 (s, 9H), 1.65-1.94 (m, 4H), 3.07-3.15 (m, 1H), 4.46-4.54 (m, 1H), 4.88 (d, J=2.3 Hz, 1H), 5.29 (d, J=4.5 Hz, 1H), 6.83-6.89 (m, 2H), 7.07-7.17 (m, 4H), 7.19-7.25 (m, 2H), 7.27-7.34 (m, 4H) ppm.

Example 7

Preparation of (3R,4S)-1-(4-Fluorophenyl)-3-[(S)-3-(4-fluorophenyl)-3-hydroxypropyl]-4-(4-hydroxyphenyl)-azetidin-2-one (I, ezetimibe)

5.0 g (9.6 mmol) (3R,4S)-4-[4-(tert-butyl-dimethyl-silanyl-oxy)-phenyl]-1-(4-fluorophenyl)-3-[(S)-3-(4-fluorophenyl)-3-hydroxypropyl]-azetidin-2-on (XI, R4=TBDMS) was solved in 35 ml 2-propanol and 10 ml 2M sulphuric acid solution is added. The solution is heated at 60-70° C. for 1-2 h, and then it was allowed to cool. The product was crystallized by adding ion-free water. The crystalline product was filtered out and washed with water to neutral.

Yield: 3.2 g (81%, together the steps 7. and 8.)

$^1$H NMR data: (500 MHz, DMSO-$d_6$, 25° C.) δ 1.65-1.92 (m, 4H), 3.05-3.13 (m, 1H), 4.46-4.55 (m, 1H), 4.81 (d, J=2.3 Hz, 1H), 5.29 (d, J=3.7 Hz, 1H), 6.74-6.80 (m, 2H), 7.08-7.17 (m, 4H), 7.19-7.26 (m, 4H), 7.28-7.35 (m, 2H), 9.54 (s, 1H) ppm.

Example 8

Preparation of (E)-[4-(tert-butyl-dimethyl-silanyloxy)-benzylidene]-(4-fluorophenyl)-amine (VIIa)

21.5 g (0.1 mol) (E)-(4-hydroxy-benzylidene)-(4-fluorophenyl)-amine (VIIb) is dissolved in 125 ml water-free tetrahydrofuran, 10.2 g (0.15 mol) imidazol is added to the solution, and then 40 ml tetrahydrofuranic solution of 18.8 g (0.125 mol) tert-butyl-dimethyl-silil-chloride is added dropwise into it at 20-25° C. The reaction mixture was stirred at this temperature while the starting material could not be detected in the reaction mixture by thin-layer chromatography. The expected reaction time is 1-2 h. The reaction mixture was diluted with 50 ml toluene, and it was poured onto 100 ml water. The aqueous phase was extracted with 50 ml toluene, and then the united organic phase was washed with 3×50 water to neutral. The solution was evaporated and the product was crystallized from cool n-hexane.

Yield: 28 g (85%).

The invention claimed is:

1. A process for the preparation of ezetimibe of the Formula I

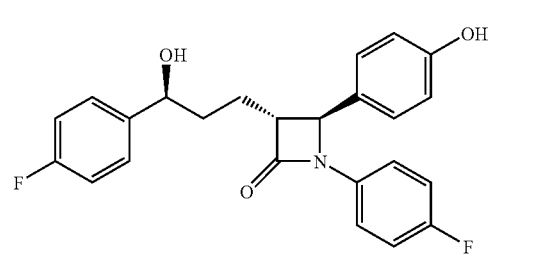

comprising the following steps:

a) converting 4-(4-fluorobenzoyl)-butyric acid of the Formula II into 4-[2-(4-fluorophenyl)-[1,3]dioxolane-2-yl]-butyric acid of the Formula IV through a non-isolated intermediate of Formula III,

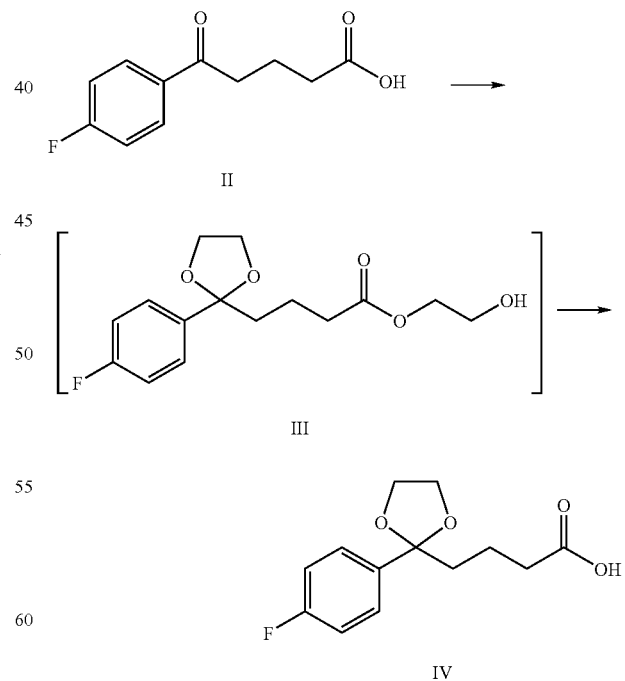

b) acylating a chiral compound of Formula V with the compound of Formula IV to obtain an acylated oxazolidinone derivative of the Formula VI,

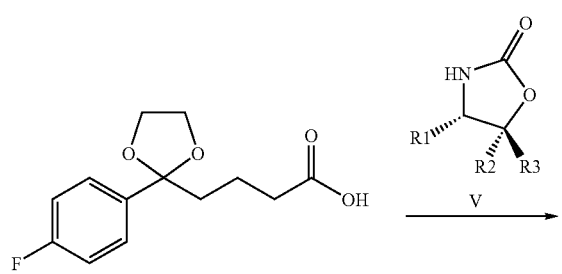

IV

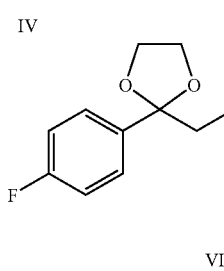

VI where the compound of Formula V is selected from the compounds of the Formulas Va, Vb, Vc, or Vd

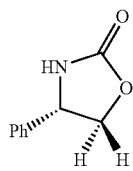

Va

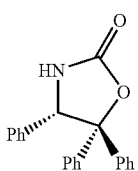

Vb

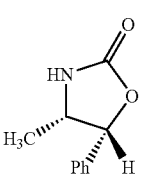

Vc

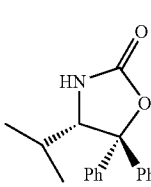

Vd and wherein R1, R2 and R3 represent:
in case of Va: R1=Ph, R2=R3=H,
in case of Vb: R1=R2=R3=Ph,
in case of Vc: R1=methyl, R2=Ph, R3=H and
in case of Vd: R1=isopropyl, R2=R3=Ph,
and where Ph represents phenyl group c) reacting the acylated oxazolidinone compound of Formula VI with a protected imine compound of Formula VII, and isolating the compound of Formula VIII, where R4 represents a silyl protecting group,

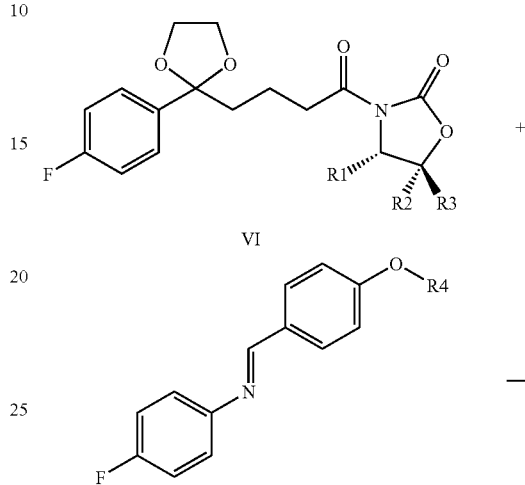

VI

VII

VIII cyclizing the compound of Formula VIII to obtain the protected azetidinone derivative of general Formula IX,

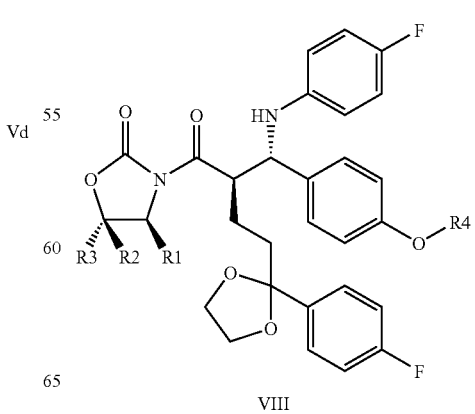

VIII

-continued

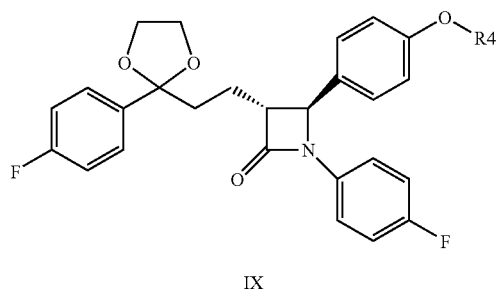

IX d) hydrolizing the ketal group of the compound of Formula IX to obtain a compound of Formula X,

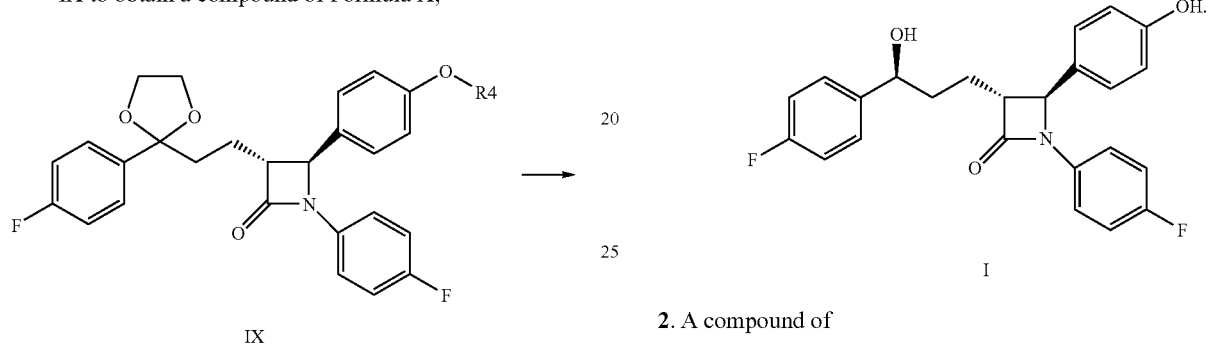

e) reducing enantioselectively the compound of general Formula X to obtain the compound of Formula XI,

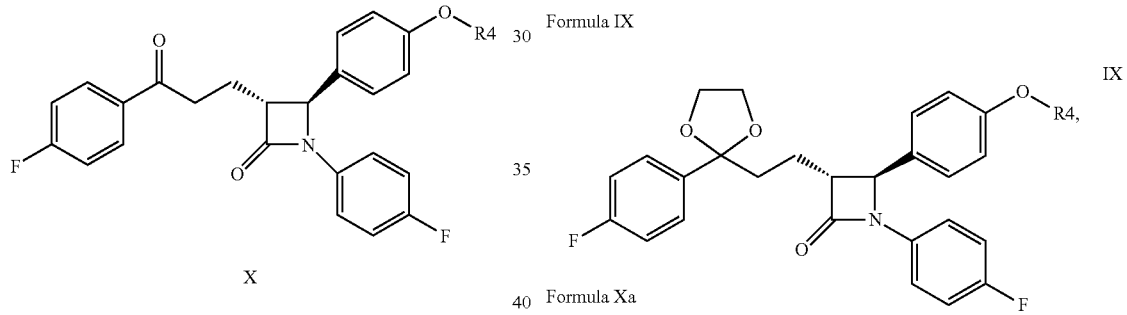

f) removing the silyl protecting group of the compound of the general Formula XI to obtain the end-product ezetimibe of the Formula I

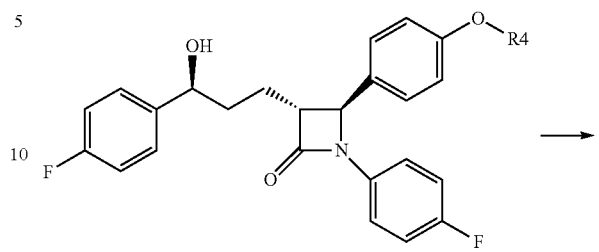

2. A compound of Formula IX

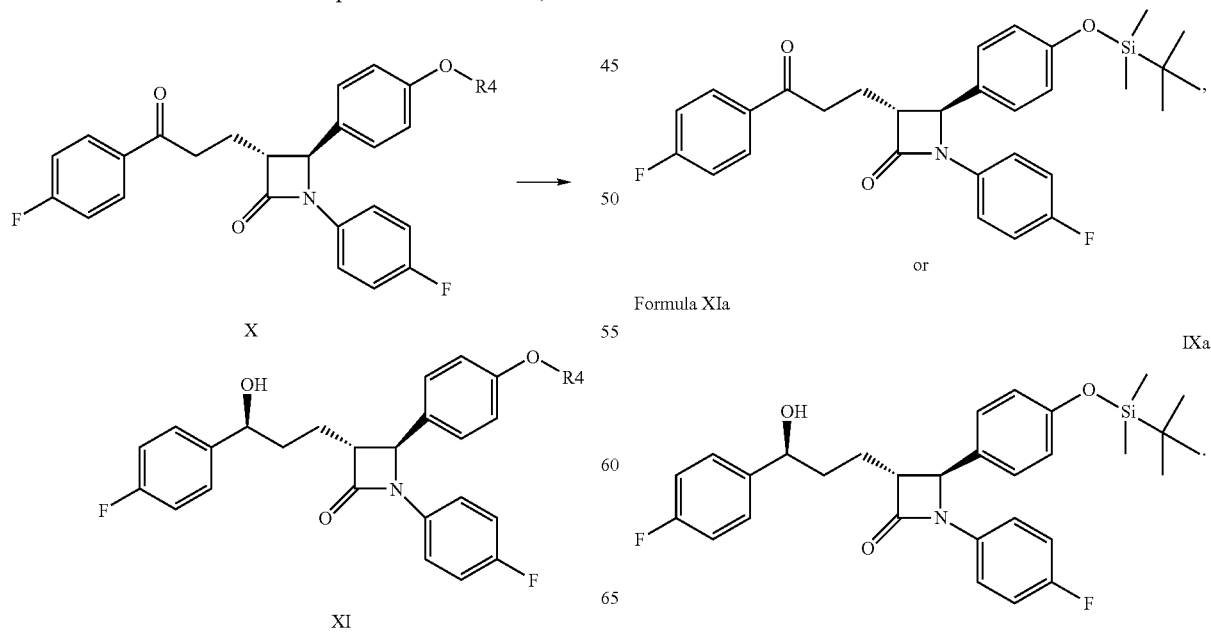

wherein

R4 is a silyl protecting group.

3. The compound of claim 2, which is of Formula IX.

4. The compound of claim 2, which is of Formula Xa.

5. The compound of claim 2, which is of Formula XIa.

6. The process of claim 1 wherein in step a) the 4-(4-fluorobenzoyl)-butyric acid of the Formula II is reacted with ethylene glycol to convert it into the compound of the Formula III which is hydrolyzed by a base solution to form 4-[2-(4-fluoro-phenyl)-[1,3]dioxolane-2-yl]-butyric acid of the Formula IV.

7. The process of claim 1 wherein R4 represents a tert-butyl-dimethyl-silyl group.

8. The compound of claim 2 wherein R4 represents a tert-butyl-dimethyl-silyl group.

9. The compound of claim 3 wherein R4 represents a tert-butyl-dimethyl-silyl group.

10. The compound of claim 3 wherein R4 represents a tert-butyl-dimethyl-silyl group or a tert-butyl-diphenyl-silyl group.

* * * * *

UNITED STATES PATENT AND TRADEMARK OFFICE
CERTIFICATE OF CORRECTION

PATENT NO. : 8,178,665 B2
APPLICATION NO. : 12/097185
DATED : May 15, 2012
INVENTOR(S) : Bódi et al.

Page 1 of 1

It is certified that error appears in the above-identified patent and that said Letters Patent is hereby corrected as shown below:

Claim 2, at column 26, line 56, of the patent, "IXa" should read -- XIa --.
Claim 2, at column 26, line 59, of the patent, the "." at the end of the line should be a -- , --.

Signed and Sealed this
Thirty-first Day of July, 2012

David J. Kappos
*Director of the United States Patent and Trademark Office*